United States Patent
Adelinet (10) Patent No.: US 10,394,976 B2
(45) Date of Patent: Aug. 27, 2019

(54) METHOD OF EXPLOITING HYDROCARBONS FROM A SEDIMENTARY BASIN COMPRISING CARBONATE ROCKS, BY MEANS OF STRATIGRAPHIC SIMULATION

(71) Applicant: IFP Energies nouvelles, Rueil-Malmaison (FR)

(72) Inventor: Mathilde Adelinet, Rueil-Malmaison (FR)

(73) Assignee: IFP ENERGIES NOUVELLES, Rueil-Malmaison (FR)

(*) Notice: Subject to any disclaimer, the term of this patent is extended or adjusted under 35 U.S.C. 154(b) by 303 days.

(21) Appl. No.: 15/376,154

(22) Filed: Dec. 12, 2016

(65) Prior Publication Data
US 2018/0163516 A1 Jun. 14, 2018

(51) Int. Cl.
*G06F 17/50* (2006.01)
*G01N 33/24* (2006.01)
*E21B 43/00* (2006.01)
*G01N 21/84* (2006.01)
*G01N 24/08* (2006.01)

(52) U.S. Cl.
CPC .......... *G06F 17/5009* (2013.01); *E21B 43/00* (2013.01); *G01N 33/24* (2013.01); *G01N 21/84* (2013.01); *G01N 24/081* (2013.01); *G01N 2223/616* (2013.01)

(58) Field of Classification Search
USPC ....................................................... 703/6, 10
See application file for complete search history.

(56) References Cited

U.S. PATENT DOCUMENTS

2018/0031732 A1* 2/2018 Mosse .................. G01V 99/005

OTHER PUBLICATIONS

Bernard P. Boudreau, Diagenetic Models and Their Implementation Modelling Transport and Reactions in Aquatic Sediments, Department of Oceanography Dalhousie University Halifax, NS B3H 4J1, ISBN-13:97S-3-642-64399-6 (Year: 2003).*

* cited by examiner

*Primary Examiner* — Aniss Chad
(74) *Attorney, Agent, or Firm* — Fitch, Even, Tabin & Flannery LLP (57) ABSTRACT

A method of exploiting hydrocarbons from a sedimentary basin comprising at least one layer of carbonate sediments, by use of stratigraphic simulation is disclosed from measurements carried out on a rock sample from a carbonate layer of the basin studied, a series of diagenetic stages undergone by the sediments, the parameters of the microstructural model representative of the final diagenetic state of sediments, and minimum and maximum variations of the parameters for each diagenetic stage are determined. The mechanical parameters of the sediments of the layer are subsequently determined for each the diagenetic stage, using effective medium modelling and microstructural model parameter variations determined for each of the stages. The mechanical parameters which are taken into account for each diagenetic stage in a stratigraphic simulation in order to assess the petroleum potential of the basin studied.

24 Claims, 4 Drawing Sheets

METHOD OF EXPLOITING HYDROCARBONS FROM A SEDIMENTARY BASIN COMPRISING CARBONATE ROCKS, BY MEANS OF STRATIGRAPHIC SIMULATION

BACKGROUND OF THE INVENTION

Field of the Invention

The present invention relates to petroleum reservoir or geological gas storage site exploration and exploitation.

Description of the Prior Art

Petroleum exploration seeks hydrocarbon reservoirs within a sedimentary basin. Understanding the principles of hydrocarbon genesis and the connections thereof with the subsurface geological history has allowed development of methods for assessing the petroleum potential of a sedimentary basin. The general procedure for assessing the petroleum potential of a sedimentary basin shuttles between a prediction of the petroleum potential of the sedimentary basin, available data relative to the basin being studied (outcrops, seismic surveys, drilling data for example), and exploratory drilling operations in the various zones having the best potential, in order to confirm or invalidate the previously predicted potential and to acquire new data useful for new and more precise studies.

Petroleum reservoir exploitation selects, from data collected during the petroleum exploration phase, the reservoir zones with the best petroleum potential, defines optimum exploitation schemes for these zones (using reservoir simulation for example in order to define the number and positions of the exploitation wells allowing optimum hydrocarbon recovery), and drilling exploitation wells. In general, necessary production infrastructures are put in place necessary for reservoir development.

In some sedimentary basins having a complicated geological history involving many physical processes, or when the volume of data is very large, petroleum potential assessment of a sedimentary basin generally requires software tools (softwares executed by a computer) allowing synthesis of the available data, as well as software tools allowing simulation of the geological history and of the many physical processes that govern it. This procedure is referred to as "basin modelling". The family of softwares referred to as basin modelling softwares allows simulation in one, two or three dimensions the sedimentary, tectonic, thermal, hydrodynamic, organic and inorganic chemical processes involved in the formation of a petroleum basin.

Concerning more particularly the sedimentary processes, tools are used involving a set of equations simulating the sedimentary evolution of a basin over geological times, that is from sediment deposition to a current time. Simulation of the sedimentary history of a basin requires accounting for various parameters: (1) the assessment of the space available for sedimentation, linked with tectonic and/or eustatic movements, (2) the sediment supply to the basin, either through boundaries, or through the agency of in-situ production or precipitation, (3) the transport of these sediments in the available space, and (4) the evolution of these sediments during burial, which is referred to as diagenesis. This type of simulation, referred to as "stratigraphic simulation," notably allows testing different hypotheses about the sedimentary processes that have affected the basin and updating these hypotheses by comparing the simulation results obtained with the observed current state of the sedimentary deposits of a basin. The DionisosFlow® software (IFP Energies nouvelles, France) is an example of such a software, referred to as stratigraphic simulator, implementing stratigraphic simulation.

Diagenesis thus is one of the major sedimentary processes in the history of a sedimentary basin. Diagenesis is the chemical, biochemical and physical changes affecting sediments that have settled in a basin as compact sedimentary rocks. Indeed, the sediments that settle in a sedimentary basin are loose and water rich. As they are progressively buried in the basin, these sediments undergo pressure and temperature conditions leading to their transformation. This transformation generally occurs in shallow environments and in several stages that vary according to the nature of the sediments and the burial conditions.

In comparison with elastic sedimentary rocks of sandstone or clay type, the diagenesis of carbonate rocks is generally complex and it can notably have many chemical and/or biological processes linked together. As diagenesis increases with time and depth, it is characterized by (1) the compaction of the sediments with loss of water (mechanical packing linked with the weight of the layers deposited above the sediments. This process tends to reduce the porosity of the rock and to increased points of contact between grains), (2) an increase in the burial temperature, which promotes chemical reactions, and (3) a multiplication of various complex reactions such as: the transformation (or epigenization) of some minerals to other minerals (dolomitization for example), the dissolution of grains at their contact points and the precipitation (cementation) in inter-grain spaces. Furthermore, each carbonate rock of each basin undergoes specific diagenetic stages, and the intensity of each stage can even vary from one point of the basin being considered to another. This is referred to a diagenetic path, which can be more or less complex.

The following documents are mentioned in the description:

Adelinet, M., Fortin, J., & Gueguen, Y., 2011 a. Dispersion of Elastic Moduli in a Porous-Cracked Rock: Theoretical Predictions for Squirt-Flow. *Tectonophysics*, 503(1), 173-181.

Adelinet, M., Dorbath, C., Le Ravalec, M., Fortin, J., & Gueguen, Y., 2011b. Deriving Microstructure and Fluid State Within the Icelandic Crust From the Inversion of Tomography Data. *Geophysical Research Letters*, 38(3).

Granjeon, D. & Joseph, P., 1999. Concepts and Applications of a 3-D Multiple Lithology, Diffusive Model in Stratigraphic Modeling. *Numerical Experiments in Stratigraphy Recent Advances in Stratigraphic and Sedimentologic Computer Simulations SEPM Special Publications No 62.*

Xu, S., & Payne, M. A. (2009). Modeling Elastic Properties in Carbonate Rocks. *The Leading Edge*, 28(1), 66-74.

The processes involved in the diagenesis of a carbonate rock result in a change in the microstructural parameters of a rock (nature and geometry of the grains forming the matrix of the rock; nature and geometry of the pores of the rock). In fact, the mechanical properties of the carbonate rock are affected by the chemical and/or biological processes that take place during diagenesis. Thus, the diagenetic transformations undergone by a rock over time result in a variation over geological times in the mechanical properties of the rocks (elastic moduli) and, a fortiori, in their petrophysical properties (porosity, permeability for example).

To date, limited consideration is given to diagenesis in stratigraphic computer simulation tools since only the impact of sedimentary compaction on the mechanical parameters is numerically simulated. Thus, Granjeon & Joseph in 1999 describes conventional compaction laws that relate the sediment porosity to the burial, thus allowing the volume of the sedimentary layers to be quantified. Although, such a restriction can be satisfactory (that is producing a simulation result sufficiently close to reality) for elastic type sedimentary rocks, it cannot lead to a satisfactory simulation of the diagenesis of carbonate rocks.

Now, carbonate rocks represent over 50% of the reservoir rocks currently exploited worldwide. It is therefore important to be able to properly take into account the diagenesis phenomenon in its complexity in the case of sedimentary basins comprising carbonate rocks. Notably, it seems important account for in a stratigraphic simulation the diagenesis-induced evolution over time of the mechanical parameters of a carbonate rock.

The document (Xu and Paine, 2009) discloses a method for determining mechanical properties of a carbonate rock from experimental measurements. More precisely, the mechanical properties are determined from a microstructure model by testing various values of the parameters thereof (flattening and porosity increase). These tests do however not consider an evolution over time of the parameters of the microstructural model, and therefore of the mechanical parameters of the carbonate rocks.

Adelinet et al., in 2011 a concern a method for determining structural properties of a basaltic rock from measurements carried out in the field and an effective medium representation. Effective medium modelling allows, from a fine description of the microstructure of a rock on the scale of a Representative Volume Element (RVE), to calculate homogenized mechanical properties on the scale of this volume. Seismic tomography data are used to invert two microstructural parameters of the effective model which are the crack density and the bulk modulus of the fluid filling the porosity inclusions. They do not consider an evolution over time of the parameters of a microstructural model, and therefore of the mechanical parameters of the rock being considered.

SUMMARY OF THE INVENTION

The present invention is a method for determining an evolution of the mechanical parameters of a carbonate rock over the different stages of the diagenesis undergone within a sedimentary basin. These parameters are then accounted for in a stratigraphic simulation in order to contribute to better understanding of a sedimentary basin comprising carbonate rocks, and therefore to a more reliable petroleum assessment of this type of basin.

The present invention relates to a method for oil exploitation in a sedimentary basin, the basin comprising at least one layer of carbonate sediments. Using a stratigraphic simulator allows reconstruction of the sedimentary history of the basin from a geological time t to a current time, by use of at least one rock sample from the layer and of a Representative Volume Element scale, which is determined as a function of the sample. The method comprises the following stages for the layer:

A. determining from measurements carried out on the sample, parameters of a microstructural model representative of the diagenetic state of the layer at the current time with the parameters of the microstructural model being defined on the scale;

B. identifying from measurements carried out on the sample, at least one diagenetic stage undergone by the sediments of the layer from the geological time t to the current time, and determining minimum and maximum variations of the parameters of the microstructural model for each diagenetic stage;

C. determining at least one mechanical parameter of the sediments of the layer for each of the diagenetic stages, using effective medium modelling and the variations of the parameters of the microstructural model determined for each of the diagenetic stages;

and the following stages:

D. assessing the petroleum potential of the basin at least by use of the simulator and of the mechanical parameters determined for each of thediagenetic stages, and selecting at least one zone of the basin with the highest the petroleum potential; and E. exploiting the basin as a function of the selected zone.

Preferably, the measurements can use measurements characterizing the rock carried out with a microscope, by X-ray diffraction or by porosimetry.

According to an embodiment of the invention, the microstructural parameters can include the flexibility of the interfaces between grains of the rock.

According to an embodiment of the invention, the flexibility can be supposed to not variable during the diagenetic stages.

According to an embodiment of the invention, at least one of the parameters of the microstructural model can be determined by inverse modelling.

Preferably, the minimum and maximum variations can be determined from measurements carried out on a number of samples of the rock at least equal to the number of the diagenetic stages.

Advantageously, the minimum and maximum variations can be determined from the microporosity, the macroporosity and the mineralogical composition.

According to an embodiment of the invention, from the mechanical parameters determined for each of the diagenetic stages, the permeability of the layer can be determined for each of the diagenetic stages.

According to an embodiment of the invention, from the mechanical parameters determined for each of the diagenetic stages, a synthetic seismic data cube can be determined for each of the diagenetic stages.

Preferably, in stage D, at least one process selected from among the tectonic, thermal, hydrodynamic, organic and inorganic chemical processes that have affected the basin can additionally be simulated.

Advantageously, in stage E, at least one exploitation and/or exploration well can be drilled in the selected zones for recovery of the hydrocarbons present in the basin.

Furthermore, the invention relates to a computer program product downloadable from a communication network and/or recorded on a non-transient computer-readable storage medium and/or processor executable, comprising program code instructions for implementing the method according to the description above, when the program is executed on a computer.

BRIEF DESCRIPTION OF THE DRAWINGS

Other features and advantages of the method according to the invention will be clear from reading the description hereafter of embodiments given by way of non-limitative example, with reference to the accompanying figures wherein.

DETAILED DESCRIPTION OF THE INVENTION

The following definitions are used in the description of the invention:

Effective medium modelling is physical modelling allowing assessing the effective properties of a medium from the local properties of its constituents;

Representative Volume Element of a medium is a volume of sufficiently large size to be able to define homogeneous properties representative of the medium being studied;

Carbonate inclusions are solid elements making up a carbonate rock which can be bioclasts (fossil pieces of animal or vegetable origin, most often in form of fragments) or ooliths (spheres consisting of a nucleus and various envelopes);

Thin section study is from a rock sample thinned until it is transparent with the microstructure of the rock being observed by an optical microscope using transmitted light;

Microstructural model is a simplification of the microstructure, using microscopy techniques for example, for translation into an effective medium model. The description of a microstructural model comprises at least a characterization of the mineral matrix (nature and geometry of the grains forming the matrix) and characterization of the porosity inclusions (nature and geometry of the pores). The nature of the mineral matrix is understood to be the lithologic nature of the grains (quartz, clays, limestone for example). The geometry of the grains forming the matrix is understood to be the shape of the grains of the matrix (more or less flattened ellipsoids). By nature of the pores, it is intended to distinguish between the crack porosity, dissolution porosity, etc. The geometry of the pores is understood to be the shape of the pores (coin-like shaped cracks for example, or ellipsoids for equant pores).

Mechanical parameters or properties are elastic moduli defined in continuous media mechanics. The elastic behaviour of an isotropic and linear homogeneous material is characterized by two independent elastic moduli (bulk and shear moduli) that are intrinsic constants of the material.

The invention relates to a method for oil exploitation in a sedimentary basin comprising at least one layer of carbonate sediments. In particular, the invention relates to modelling, within a stratigraphic simulation, the diagenesis phenomenon undergone by carbonate sediments. An important stage of the method according to the invention is the mechanical characterization of the diagenesis phenomenon undergone by the carbonate sediments of the basin being studied. A method for oil exploitation in a sedimentary basin is understood to be a method allowing exploitation of the hydrocarbons present within the sedimentary basin.

The present invention requires:

A stratigraphic simulator according to the prior art. A stratigraphic simulator is a software designed to reconstruct the sedimentary processes that have affected the basin from a geological time t to the current time. Simulation of the sedimentary history of a basin requires developing systems of equations allowing appraising: (1) the space available for sedimentation, linked with tectonic and/or eustatic movements, (2) the sediments supplied to the basin, either through the boundaries or through in-situ production or precipitation, (3) the transport of these sediments in the available created space and (4) the evolution of these sediments during burial, that is diagenesis. A stratigraphic simulator according to the prior art is understood to be a stratigraphic simulator modelling diagenesis through the sediment compaction phenomenon alone;

At least one rock sample for each carbonate sediment layer of the sedimentary basin being studied which can be taken in situ, by example core drilling;

Defining a Representative Volume Element (RVE) scale. The scale of an RVE is a function of the size of the rock samples available. The goal is to overcome microstructural elements likely to disturb the volume representatively (large crack running through the sample, holes not associated with a porosity in the entire sample, etc.).

The present invention comprises at least the following stages:
1. Mechanical characterization of diagenesis
    1.1 Determining the parameters of a microstructural model of the current diagenetic state
    1.2 Identifying the different diagenetic stages
    1.3 Determining the minimum and maximum variations of the microstructural model parameters for each diagenetic stage
    1.4 Determining the mechanical parameters by effective medium modelling for each diagenetic stage
2. Petroleum potential assessment
3. Sedimentary basin exploitation The main stages of the present invention are detailed hereafter. They are illustrated with a (non-limitative) example of a diagenetic path undergone by a given layer made up of carbonate sediments.

1. Mechanical Characterization of Diagenesis

The object of this first stage is the mechanical characterization of the diagenesis that has affected the carbonate sediment layers of the sedimentary basin being studied. This stage can be broken down, by way of non: limitative example, into four substages applicable in parallel or sequentially to each carbonate sediment layer of the basin being studied. These four substages are detailed for a given carbonate sediment layer.

1.1 Determining the Parameters of a Microstructural Model of the Current Diagenetic State This substage determines the parameters of a microstructural model representative of the current diagenetic state of the carbonate sediment layer being considered from experimental measurements carried out on at least one rock sample from the layer considered. According to the invention, the microstructural model parameters are defined on the scale of a Representative Volume Element (RVE) to be able to exploit these parameters through an effective medium approach in substage 1.4 described below.

A rock sample taken for example by core drilling allows obtaining the microstructural model parameters of the final diagenetic state of the rock being studied. Indeed, some stages of the formation process of the rock taken at the current time are only visible as traces or geometric elements (mineralogical phase included in or surrounding another one for example).

Thus, in this stage, measurements are carried out on a sample taken at the current time in order to determine the microstructural parameters representative of the mineral matrix (nature and geometry of the grains forming the matrix) and the microstructural parameters representative of the porosity inclusions (nature and geometry of the pores).

According to the invention, direct measurements are carried out on the sample using at least one of the following techniques:

A microscopic study performed for example with an optical microscope or a scanning electron microscope. A microscopic study allows characterizing the matrix of the rock being studied and the porosity thereof. Thus, a microscopic study allows having access to the geometry and the arrangement of the solid phases (matrix), and to the geometry and the arrangement of the rock porosity. The matrix, the crystalline inclusions and the porosity supports (spherical pores or cracks for example) can then be input at Representative Volume Element (RVE) scale;
 X-ray diffraction (XRD) performed using a diffractometer. X-ray diffraction allows quantification of the various mineralogical phases of a given sample, which allows input of a volume fraction of the solid inclusions at Representative Volume Element (RVE) scale;
 Poromosimetry performed using a nuclear magnetic resonance (NMR) spectrometer, a mercury porosimeter or a helium porosimeter. This type of measurement allows quantification of the ratio between microporosity and macroporosity at Representative Volume Element (RVE) scale.

According to an embodiment of the invention, in order to complete the microstructural model, inverse modelling can be applied from measurements on at least one sample of the carbonate rock being studied.

Indeed, carbonate rocks are often characterized by a heterogeneous mineralogical arrangement, which leads to a complexification in the mechanical response of these rocks. Some parameters of the microstructural model, notably the flexibility that exists between the various carbonate inclusions (bioclasts, ooliths for example), thus cannot be directly approximated by measurements. Quantification of these parameters can then be achieved through inverse modelling.

Inverse modelling is an iterative inversion technique. More precisely, an objective function measuring the difference between experimental data and theoretical data calculated from initial values for the parameters to be determined is constructed. Then the values of these parameters are modified iteration after iteration until a minimum is found for the objective function. Many objective function minimization algorithms are known such as the Gauss-Newton method, the Newton-Raphson method or the conjugate gradient method. According to a preferred embodiment of the present invention, the Gauss-Newton method is used.

According to an embodiment of the present invention, the experimental data of the objective function are ultrasonic measurements of the velocities of the seismic compressional waves (P waves) and of the seismic shear waves (S waves). These measurements may have been obtained in the laboratory or through a seismic acquisition survey, followed by seismic processing and scaling as presented in French patent application 2,951,555 corresponding to U.S. patent application Ser. No. 12/908,130.

According to an embodiment of the present invention, calculation of the theoretical velocities from values of the microstructural parameters at the current iteration can be obtained by effective medium modelling as described in (Adelinet et al., 2011 b).

The theoretical data are then compared with the experimental data, and inverse modelling allows minimizing the difference between these two sets of data by adjusting the values of the microstructural parameters sought.

Thus, at the end of this first substage, a microstructural model input into a Representative Volume Element (RVE), representative of the diagenetic state at the current time of the carbonate sediment layer being considered, is obtained.

1.2 Identifying the Different Diagenetic Stages

This substage identifies the different diagenetic stages undergone by the carbonate rock of the sedimentary basin being studied, from measurements carried out on at least one sample of the carbonate rock being studied. According to the invention, at least one diagenetic stage is identified. Preferably, several diagenetic stages are identified.

Figure 1:
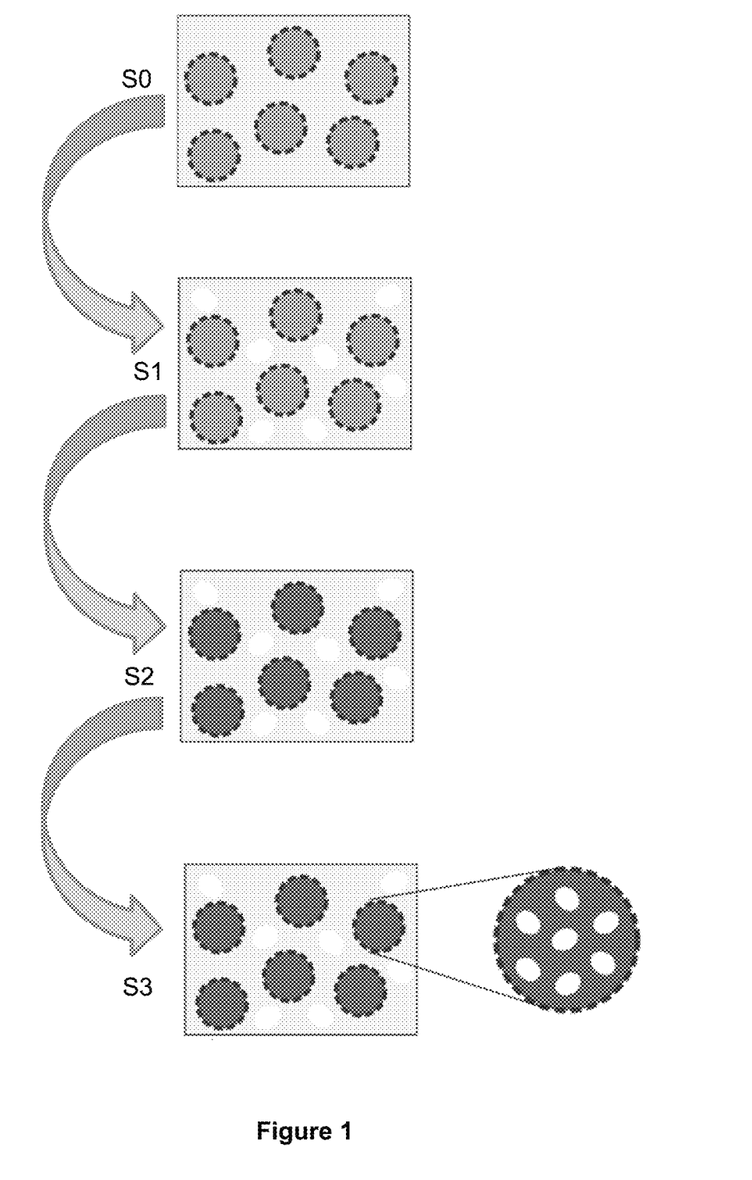
FIG. 1 illustrates an example of a diagenetic path made up of four different diagenetic stages.

While the rock samples taken at the current time provide information on a final diagenetic state regarding the mechanical properties, a fine study of the microstructure via thin sections provides information about the diagenetic history undergone by the rock. Indeed, some early stages have been only partly erased by later stages and they can therefore still be identified. From different thin sections, the carbonate geologist can identify and order the various processes undergone by the carbonate rock during the diagenesis, such as cementation, dolomitization, aragonitization or dissolution. FIG. 1 is an illustrative diagram of the diagenetic path followed by a given carbonate rock. Thus, this, figure shows a succession of images, each image simulating a microscope visualization of a sample of the rock being considered for a given diagenetic stage. The diagenetic path of the rock being considered has four diagenetic stages: a cementation stage S0 (grains shown in medium grey), a dissolution stage S1 (causing the formation of macroporosity represented by white ellipses), a dolomitization stage S2 (causing replacement of the calcite minerals by dolomite) and a dissolution stage S3 (causing the formation of microporosity represented by white intra-grain ellipses).

1.3 Determining the Minimum and Maximum Variations of the Microstructural Model Parameters for Each Diagenetic Stage This substage determines the variation boundaries of the microstructural model parameters determined in stage 1.1 for each diagenetic stage identified in stage 1.2.

For this stage, it is assumed that a sample of the carbonate layer being considered, or even part of a sample, has not undergone the same state of diagenetic progress as another sample of this layer or another part of a sample respectively. Thus, the microstructural parameter measurements may be different from one sample to another, or from one part of a sample to another. According to the invention, the minimum and maximum values of the microstructural model parameters are determined from measurements carried out on at least one rock sample of the carbonate rock. Preferably, the minimum and maximum values of the microstructural model parameters are assessed with several samples so as to take advantage of the measurement dispersion. Preferably, the minimum and maximum values of the microstructural model parameters are determined from a number of rock samples at least equal to the number of diagenetic stages identified in stage 1.2.

According to the invention, the measurements used for determining the minimum and maximum values of the mechanical parameters are carried out using at least one of the techniques described in stage 1.1 (i.e. microscopic study, X-ray diffraction, porosimetry). In particular, the thin section study allows quantification of the microstructural parameters such as the replacement of calcite crystals by dolomite crystals, the incomplete filling of a porosity by a mineral phase.

According to an embodiment of the invention, at least one variation boundary is set for at least one mechanical parameter at a predetermined value. For example, if a sample or the number of samples available do not enable access to a variation boundary of one of the mechanical parameters, this boundary from existing databases can be set from their general knowledge, etc.

According to a preferred embodiment of the invention, at least the minimum and maximum values of the microporosity, the macroporosity, and the mineralogical composition are identified.

Figure 2A:
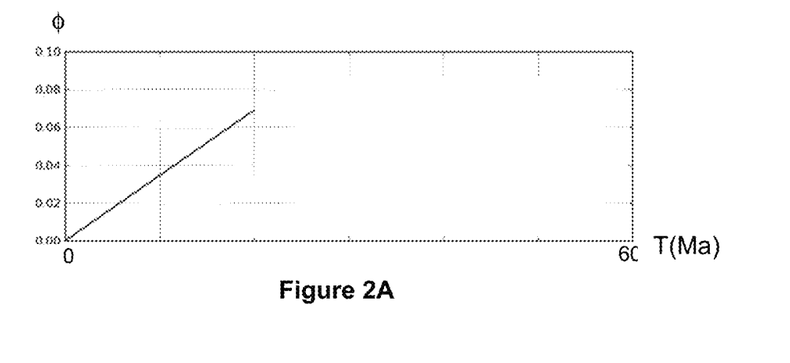
FIGS. 2A-2C show the diagenetic evolution of the microstructural parameters associated with the example shown in FIG. 1, with FIG. 2A showing evolution of porosity (I), FIG. 2B showing the evolution of ratio R, and FIG. 2C showing the evolution of porosity during diagnostic stage S3.
Figure 2B:
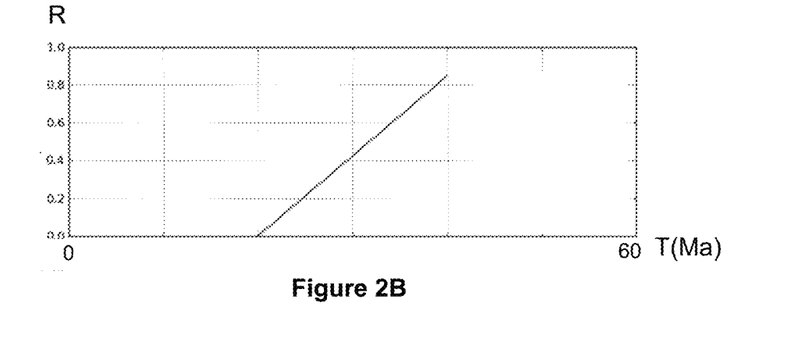
Figure 2C:
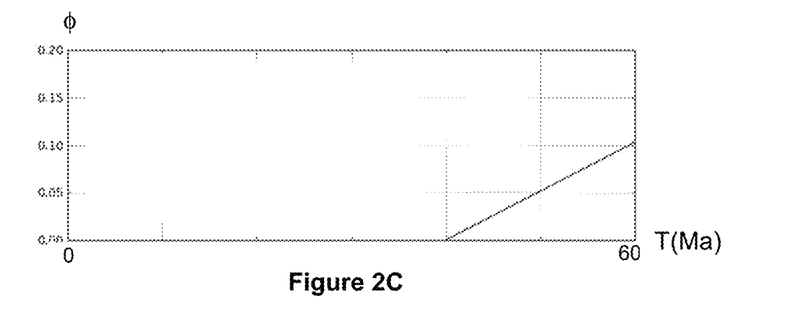

Varying the microstructural model parameters between these minimum and maximum values over time (the duration of each diagenetic stage can be arbitrarily selected) allows obtaining the evolution of the microstructural model parameters during the various diagenetic stages of the diagenetic path established in stage 1.2 above. Thus, FIGS. 2A-2C show the evolution, during diagenesis, of the microstructural parameters associated with the example shown in FIG. 1. More precisely, FIG. 2A shows the evolution of (macro) porosity $\phi$ (unitless quantity ranging between O and 1) during diagenetic stage S1, FIG. 2B shows the evolution of ratio R (unitless quantity ranging between O and 1) of replacement of the calcite by dolomite during diagenetic stage S2, and FIG. 2C shows the evolution of (micro) porosity during diagenetic stage S3.

According to an embodiment where the microstructural model comprises the interface flexibility between grains (see stage 1.1). This flexibility is assumed to be invariant during the diagenetic stages.

1.4 Determining the Mechanical Parameters by Effective Medium Modelling for Each Diagenetic Stage This stage is from the microstructural parameters defined in stage 1.1 and from the evolution of these parameters during the various diagenetic stages determined in stage 1.3, determines at least one mechanical parameter of the carbonate rock being studied by effective medium modelling, for each diagenetic stage identified in stage 1.2. Preferably, in the case of an isotropic rock, two mechanical parameters are determined which are the bulk modulus and the shear modulus.

Effective medium modelling allows, from a fine description of the microstructure of a rock at Representative Volume Element (RVE) scale, to calculate the homogenized mechanical properties. Since the evolution of the microstructural parameters has been determined for the various diagenetic stages that are identified, the mechanical properties are directly calculated by homogenization for each stage of the diagenetic path. This calculation is based on the solution of Eshelby's problem, that is the solution of the first-order perturbation induced by the presence of an ellipsoidal inclusion in a matrix.

Figure 3A:
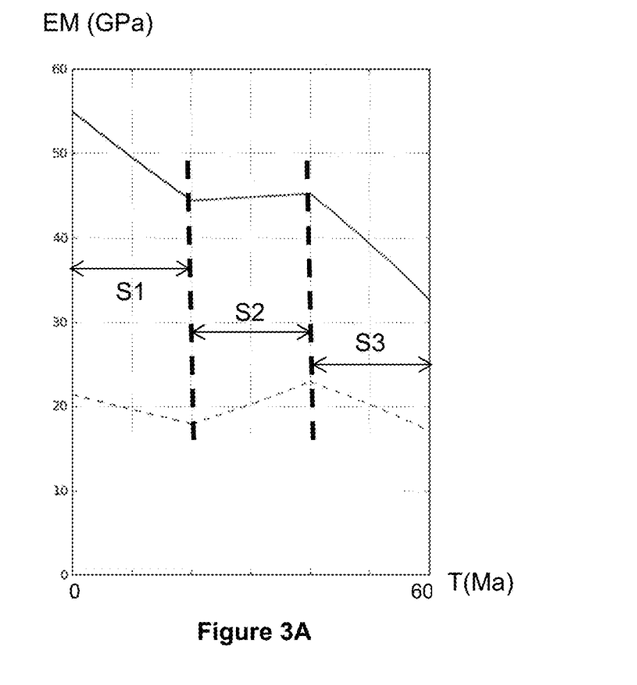
FIG. 3A shows a full line of the evolution during diagenesis of the bulk modulus and a dotted line of evolution during the diagenesis of shear modulus and FIG. 3B provides a full line showing S waves and in dotted line the evolution of the elastic moduli and of the elastic velocities as a function of the diagenetic stages determined for the example shown in FIG. 1.
Figure 3B:
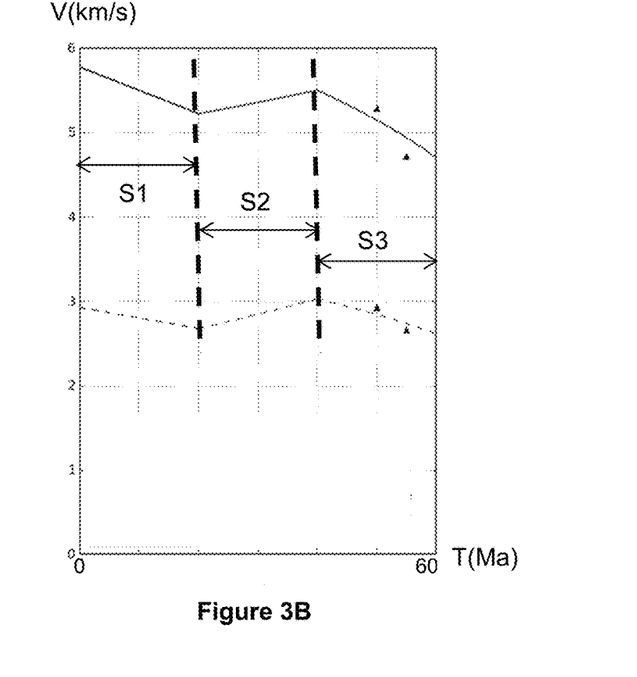

In the example shown in FIG. 1, several inclusions are present in the matrix. The problem is therefore referred to as auxiliary Eshelby's problem. In this case, mean calculation methods are used to calculate the mechanical parameters of the medium. These calculations are carried out in an isotropic case and two independent elastic moduli EM are calculated along the diagenetic path. Thus, FIG. 3A shows in full line the evolution during diagenesis of the bulk modulus, which is a constant specific to the material being studied, relating the stress to the deformation ratio of an isotropic material subjected to isostatic compression. FIG. 3A also shows in dotted line the evolution during diagenesis of the shear modulus, which is a constant intrinsic to the material being studied, that is involved in the characterization of the deformations caused by shear strains relating the stress to the deformation ratio of an isotropic material subjected to an isostatic compression. Furthermore, from the evolution of the elastic moduli during diagenesis and by solving Christoffel's equation, it is possible to deduce the evolution of velocities V of the seismic P waves (curve in full line in FIG. 3B) and S waves (curve in dotted line in FIG. 3B) during diagenesis. According to an embodiment of the present invention, the coherence between the modelling result obtained with the present invention and the experimental measurements representative of the terminal diagenetic stage is checked in this stage. Thus, FIG. 3B shows with triangles the seismic P and S wave velocity measurements carried out in the laboratory (ultrasonic measurements for example) on rock samples.

Figure 4:
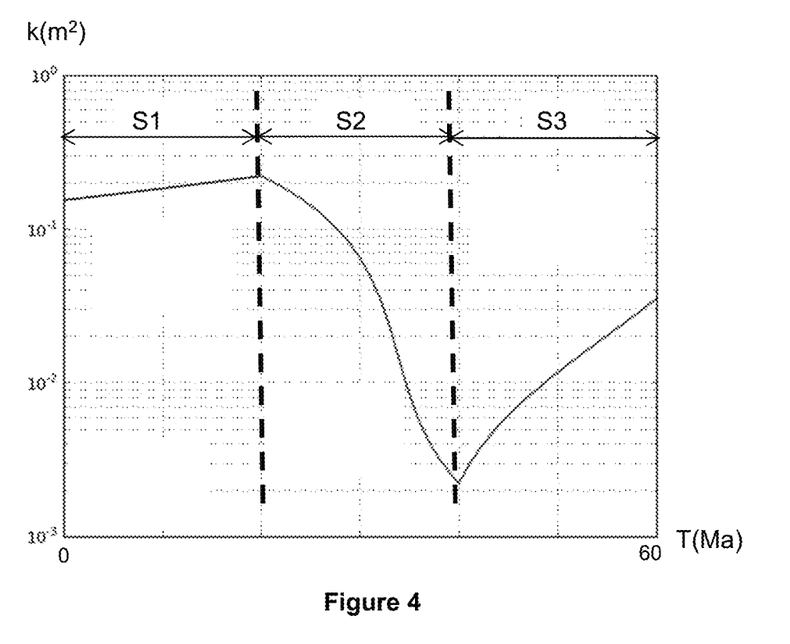
FIG. 4 shows the evolution of permeability during the diagenetic stages determined for the example shown in FIG. 1.

According to another embodiment of the present invention, from mechanical properties assessed for each stage of the diagenetic path, the permeability of the carbonate rock is determined for each stage of the diagenetic path. The effective medium models initially provided as mechanical properties are therefore converted to permeability, which gives access to the evolution of permeability k during the various diagenesis stages, as shown in FIG. 4. Perfect knowledge of methods for converting mechanical parameters to permeability is known.

According to another embodiment of the present invention, from the mechanical properties determined for each stage of the diagenetic path, seismic data cubes referred to as synthetic are constructed for each identified diagenetic stage. A seismic impedance cube is therefore constructed for each diagenetic stage, from the mechanical properties determined for the stage being considered. A seismic data simulation technique allowing these impedance cubes to be converted to synthetic seismic data from a seismic wavelet is then used. Perfect knowledge of methods for converting mechanical properties to seismic impedances, and for converting seismic impedances to synthetic seismic data is known. The synthetic seismic data cube obtained with the present invention for the final diagenetic stage can then be compared with a real seismic data cube. Depending on the conclusions of this comparison, it can be deduced whether some hypotheses made on the stratigraphic simulation parameters are pertinent or not and, consequently, modify or not the parameters in question.

The present invention thus allows making the link between the geological and sedimentologic description of the various diagenetic stages undergone by a carbonate rock and the mechanical, and possibly petrophysical and/or seismic, properties of the rock during these different diagenetic stages.

2. Petroleum Potential Assessment

Modelling of the evolution of the mechanical parameters of a carbonate rock over time is obtained at the end of the previous stage. According to the invention, this modelling is taken into account in a stratigraphic simulation, which contributes to better understanding of the sedimentary history of the basin being studied.

Other tools of the basin modelling family can furthermore be used to simulate the tectonic, thermal, hydrodynamic, organic and inorganic chemical processes that have affected the basin studied. An example of such a basin modelling tool is the TEMISFLOW software (IFP Energies nouvelles, France).

Thus, at the end of this stage, information is known about:
i. the emplacement of the sedimentary layers,
ii. the effects of diagenesis on the deposited sediments,
iii. the heating thereof during burial,
iv. the fluid pressure changes resulting from burial,
v. the formation of hydrocarbons by thermogenesis,
vi. the displacement of these hydrocarbons in the basin under the effect of buoyancy, capillarity, and pressure gradient differences, and
vii. the amount of hydrocarbons resulting from thermogenesis.

From such information, knowledge is known of the zones of the basin comprising hydrocarbons, and of the amount, the nature and the pressure of the hydrocarbons trapped therein. Then the selection the zone(s) occurs of the basin being studied with the best petroleum potential.

3. Sedimentary Basin Exploitation

The petroleum exploitation of the basin can then take a variety of forms, notably:

exploration drilling in the various zones selected for having the best potential, so as to confirm or to invalidate the previously estimated potential and to acquire new data for supporting new and more precise studies;

definition of optimum exploitation schemes for the selected zones, for example by reservoir simulation, in order to define the number and position of the exploitation wells allowing optimum hydrocarbon recovery;

exploitation drilling (production or injection wells) for recovery of the hydrocarbons present within the sedimentary basin in the zones selected for having the best potential, and /*establishment of the production infrastructures necessary for reservoir development.

Computer Program Product

Furthermore, the invention concerns a computer program product downloadable from a communication network and/or recorded on a non-transitory computer-readable storage medium and/or processor executable, comprising program code Instructions executed on a computer for implementing the method as described above.

The invention claimed is:

1. A method for oil exploitation in a sedimentary basin including at least one layer of carbonate sediments using a stratigraphic simulator for reconstruction of sedimentary history of the basin from a geological time t to a current time by use of at least one rock sample from each layer and a representative volume element scale determined as a function of the at least one rock sample with steps being carried out for each layer comprising:

A. determining from measurements carried on each rock sample parameters of a microstructural model representative of a diagenetic state of each layer at the current time with each sample parameter of the microstructural model being defined at the scale;

B. identifying from the measurements carried out on each rock sample at least one diagenetic state undergone by sediments of each layer from the geological time t to the current time and determining minimum and maximum variations of each parameter of the microstructural model for each diagenetic state;

C. determining at least one mechanical parameter of the sediments of each layer for each diagenetic state by using medium modelling and variations of each parameter of the microstructural model determined for each diagenetic state;

D. assessing the petroleum potential of the basin at least by use of the stratigraphic simulator, determining each mechanical parameter for each diagenetic state and selecting at least one zone of the basin with a highest petroleum potential; and E. exploiting the basin in accordance with each selected zone.

2. The method as claimed in claim 1, wherein measurements characterizing the at least one rock are carried out with a microscope, by X-ray diffraction or by porosimetry.

3. The method as claimed in claim 2, wherein the microstructural parameters include flexibility of interfaces between grains of the rock.

4. The method as claimed in claim 3, wherein the flexibility of the interfaces does not vary during each diagenetic stage.

5. The method as claimed in claim 4, wherein the minimum and maximum variations are determined from measurements carried out on each sample of the rock at least equal in number to a number of the diagenetic stages.

6. The method as claimed in claim 4, wherein the minimum and maximum variations are determined from microporosity, macroporosity or mineralogical composition.

7. The method as claimed in claim 3, wherein the minimum and maximum variations are determined from measurements carried out on each sample of the rock at least equal in number to a number of the diagenetic stages.

8. The method as claimed in claim 3, wherein the minimum and maximum variations are determined from microporosity, macroporosity or mineralogical composition.

9. The method as claimed in claim 2, wherein each parameter of the microstructural model is determined by inverse modelling.

10. The method as claimed in claim 2, wherein the minimum and maximum variations are determined from measurements carried out on each sample of the rock at least equal in number to a number of the diagenetic stages.

11. The method as claimed in claim 2, wherein the minimum and maximum variations are determined from microporosity, macroporosity or mineralogical composition.

12. The method as claimed in claim 1, wherein the microstructural parameters include flexibility of interfaces between grains of the rock.

13. The method as claimed in claim 12, wherein the flexibility of the interfaces does not vary during each diagenetic stage.

14. The method as claimed in claim 12, wherein each parameter of the microstructural model is determined by inverse modelling.

15. The method as claimed in claim 12, wherein the minimum and maximum variations are determined from measurements carried out on each sample of the rock at least equal in number to a number of the diagenetic stages.

16. The method as claimed in claim 12, wherein the minimum and maximum variations are, determined from microporosity, macroporosity or mineralogical composition.

17. The method as claimed in claim 1, wherein each parameter of the microstructural model is determined by inverse modelling.

18. The method as claimed in claim 1, wherein the minimum and maximum variations are determined from measurements carried out on each sample of the rock at least equal in number to a number of the diagenetic stages.

19. The method as claimed in claim 1, wherein the minimum and maximum variations are determined from microporosity, macroporosity or mineralogical composition.

20. The method as claimed in claim 1 wherein, from each mechanical parameter determined for each diagenetic stage, permeability of the layer is determined for each diagenetic stage.

21. The method as claimed in claim 1 wherein, from each mechanical parameter determined for each diagenetic stage, a synthetic seismic data cube is determined for each diagenetic state.

22. The method as claimed in claim 1 wherein, in step D, at least one process selected from tectonic, thermal, hydrodynamic, organic and inorganic chemical processes affecting the basin is simulated.

23. The method as claimed in claim 1 wherein, in step E, at least one of an exploitation and exploration well is drilled in each selected zone for recovery of the hydrocarbons present in the sedimentary basin.

24. A computer program product recorded on a non-transitory computer-readable medium comprising instructions which when executed on a computer perform the method of steps A-D of claim 1.

\* \* \* \* \*